(12) United States Patent
Bruno et al.

(10) Patent No.: US 8,168,119 B1
(45) Date of Patent: May 1, 2012

(54) ANTI-MICROBIAL SYSTEM FOR INPUT TERMINAL

(75) Inventors: Philip J. Bruno, Oakland, CA (US); Robert A. D. Schwartz, Oakland, CA (US)

(73) Assignee: Key Source International, Oakland, CA (US)

( * ) Notice: Subject to any disclaimer, the term of this patent is extended or adjusted under 35 U.S.C. 154(b) by 263 days.

(21) Appl. No.: 12/661,081

(22) Filed: Mar. 9, 2010

(51) Int. Cl.
- *A61L 2/00* (2006.01)
- *A61L 9/01* (2006.01)
- *B08B 7/00* (2006.01)
- *G09G 5/00* (2006.01)

(52) U.S. Cl. ............ 422/28; 422/1; 422/292; 134/4; 424/76.8; 424/641; 510/108; 345/156; 455/67.11

(58) Field of Classification Search .......... 422/1, 28, 422/292; 134/4; 424/76.8, 641; 510/108; 345/156; 455/67.11
See application file for complete search history.

(56) References Cited

U.S. PATENT DOCUMENTS

| | | | |
|---|---|---|---|
| 6,358,519 B1 | 3/2002 | Waterman | |
| 6,490,351 B1 | 12/2002 | Roberts | |
| 6,750,569 B2 | 6/2004 | Liao | |
| 2004/0110562 A1 | 6/2004 | Kajino et al. | |
| 2004/0191315 A1 | 9/2004 | Slattery et al. | |
| 2005/0052410 A1* | 3/2005 | Chen | 345/156 |
| 2005/0186911 A1 | 8/2005 | Chen | |
| 2006/0188389 A1 | 8/2006 | Levy | |

* cited by examiner

*Primary Examiner* — Jill Warden
*Assistant Examiner* — Monzer Chorbaji
(74) *Attorney, Agent, or Firm* — Howard Cohen

(57) ABSTRACT

A method and apparatus disinfecting a computer keyboard includes a metal ion treatment applied to the computer keyboard and other user input devices. A further measure taken is the installation of a shutoff mechanism in the link connecting the computer keyboard to the computer system to open the data connections between the keyboard and host system. Another measure is the periodic and reiterated wipedown of the keyboard and ancillary input devices with an antiseptic wipe. The shutoff mechanism is turned off before the wipedown procedure is carried out, to prevent any incidental keyboard entries made during the wipedown process from being transmitted to the host system.

9 Claims, 3 Drawing Sheets

ANTI-MICROBIAL SYSTEM FOR INPUT TERMINAL

CROSS-REFERENCE TO RELATED APPLICATIONS

Not applicable.

FEDERALLY SPONSORED RESEARCH

Not applicable.

SEQUENCE LISTING, ETC ON CD

Not applicable.

BACKGROUND OF THE INVENTION

1. Field of the Invention

This invention relates to communicable disease vectors that emanate from data entry keyboards and input devices that are used in hospitals, medical centers, doctor's offices and the like, and, more particularly, to a system for defeating microbial growth and persistence on the surfaces of these devices.

2. Description of Related Art

According to studies done by several major universities, computer keyboards can be infected with many, many different types of microbes, scores of which can be harmful and can lead to cross-contamination infection of patients. Nearly ten percent of these patients will die as direct cause of a contracted infection. Healthcare, more and more is relying on computer technology to better treat patients. This very technology is also a threat to patient wellness during hospital visits. Healthcare professionals use shared workstation to access and input data for electronic medical records. This shared workstation environment, with many users typing away 24 hours a day, seven days a week leads to a very contaminated keyboard, which is probably, after their stethoscope the second most important tool they use throughout the course of each shift. Keeping these keyboards clean is an absolute imperative. Although the users may be gloved, it has been observed that a small but significant percentage of user interactions with data entry keyboard and devices occurs with contaminated hands, whether gloved or not.

One technique for reducing bacterial and pathogenic contamination of keyboards in a medical setting is the use of materials and surface treatments that are lethal to pathogenic bacteria and viruses. These techniques may involve the use of anti-microbial compounds added to the plastic or resin materials that comprise the keys, frame, faceplate, and other components of the keyboard. Alternatively, a surface treatment such as the deposition of ionic silver (Ag+), which fuses with the surface and provides an ongoing germicidal effect. One such treatment is known as IonArmour® from Innova Materials of Philadelphia, Pa. Other metal ions have also been employed in similar surface treatments for similar results.

The promise of metal ion treatments such as these lies in their ability to provide long-term, continuous anti-microbial action to not only prevent proliferation of bacteria and viruses on keyboards, but to actively eradicate these organisms over the course of a few hours to a few days. However persistent and effective these treatments may be, they require an extended period of time to be fully successful, and many keyboard-operated systems are in use fairly constantly, particularly in a medical setting where patient care occurs round-the-clock. Thus ongoing re-contamination by a number of users may result in communicable disease transmission, despite the active surface treatment.

An alternative technique for reducing bacterial and pathogenic contamination of keyboards involves the application of a germicidal compound directly to the keyboard surfaces, using wipes or sprayers. The germicidal compound may be any one (or combination) of several different hospital-grade disinfectants which act immediately to eliminate bacteria and viruses from the surfaces. This measure is fairly absolute in destroying micro-organisms, but is exhibits very little persistent effect. That is, after the disinfectant evaporates or is wiped dry, it is possible for contamination to be re-established fairly quickly by subsequent users or airborne contamination. This fact implies that the technique of germicidal wipe-down must be carried out frequently and regularly. In practice, this technique is not applied often enough.

Moreover, the wipe-down technique may comprise a potential threat to the security and operation of computer systems to which the keyboard is connected. It is now commonplace for hospitals and other medical facilities to require that anyone attempting to access the computer system through the keyboard must first enter some form of identifying name and password. To maintain high security and prevent entry to the system by unauthorized users, many systems have established shutoff protocols if a keyboard entries are made before a proper access name and code are input. This factor interacts with the wipe-down procedures in a negative manner: use of a germicidal wipe almost certainly causes some of the keyboard's keys to be depressed, which appears to the computer system as data entry before approved access has been granted. The system may then immediately shut down the keyboard and its associated terminal until supervisory authority is invoked to restart the terminal. As a result, the wipe-down process may seriously interfere with the computer system's terminals.

Thus it is apparent that the prior art indicates a failure to address successfully the short-term disinfection treatment of computer keyboards and other input devices to a medical facility's computer system, and to meld that treatment with long-term disinfection techniques.

BRIEF SUMMARY OF THE INVENTION

The present invention generally comprises a method and apparatus for creating and sustaining an anti-microbial environment on the surfaces of a computer keyboard and terminal, particularly in a medical facility setting. The invention includes three seemingly disparate measures that are united in their ability to maintain germicidal action during periods of use, and to exert a sustained anti-microbial action during periods of inactivity or dormancy.

One measure taken in accordance with the invention is the application of a metal ion treatment to the computer keyboard and other user input devices, hereinafter termed the computer keyboard. Generally the metal ions, such as silver ions or others high on the electromotive series, may be impregnated into the material that comprises the keyboard components. One such process involves spraying a solution of silver ions onto the manufactured keyboard components, and thereafter heating them to drive the ions into the surface of the materials (typically polymer plastic or resin). This process may provide sufficiently deep impregnation so that subsequent wear of the keyboard surface cannot remove the surface layer containing the metal ionic treatment. This treatment provides a long-term anti-microbial effect that discourages colony formation and proliferation of bacteria and viruses on the surfaces of the keyboard and input devices. Other processes involve adding silver ions into the plastic material that comprises the input devices.

A further measure taken in accordance with the invention is the provision of a shutoff in the data link that connects the computer keyboard to the computer system (terminal connection, smart terminal computer, network connection, hereinafter the host system). The shutoff may comprise a switch on the keyboard itself, or a switch installed in the cable connecting the keyboard to the computer system. The switch may comprise a simple SPST switch that opens the data connections between the keyboard and host system, whereby any incidental or accidental keyboard entries made during a switch off state will not be transmitted to the host system.

Another measure according to the invention is the periodic and reiterated wipedown of the keyboard and ancillary input devices with a cloth or paper wipe that is saturated with a hospital-grade antiseptic compound. This wipedown step provides immediate destruction of virtually all microbial contamination on the keyboard, and in the short-term disrupts all disease vectors that pass through the keyboard and its ancillary devices.

Note that the shutoff mechanism is turned off before the wipedown procedure is carried out, to prevent any incidental keyboard entries made during the wipedown process from being transmitted to the host system. This prevents the potential for a security alert and shutdown of the terminal. The switch is turned back on after the wipedown is completed, and terminal operation is resumed.

A further aspect of the invention is the provision of a method for instituting the wipedown step when it is appropriate, considering the level of bio-contamination that is being handled, the number of users of the keyboard, and the location of the keyboard. After the previous three measures have been implemented, the computer system to which the computer keyboard is operatively connected may be programmed to estimate the contamination hazard posed by the keyboard, based on a counting system which may consider the number of users since the last wipedown procedure, the current site of the keyboard (e.g., ranging from surgical operating room to publicly accessible locations), and the dormancy time (elapsed time since previous use). One method for identifying the time of previous wipedown procedure may be to consider the last time that the keyboard switch was shut off.

Thus, for example, if the computer keyboard has been wiped down and there have been no further users for some time period, a wipedown procedure may not be warranted or required. If there have been a low number of users that does not reach a threshold level, the next wipedown may be postponed. These parameters may be adjusted for the situation, and they enable the computer system to manage the anti-microbial treatments used in the medical facility. As a result, the computer system may optimize the use of wipedown procedures so they are done when necessary, minimizing the maintenance labor and the downtime of the computer terminal. It may also regard the dormancy time and the resulting action of the metal ion treatment to allow the metal ion treatment to function and reduce microbial contamination.

DETAILED DESCRIPTION OF THE INVENTION

The present invention generally comprises a method and apparatus for creating and sustaining an anti-microbial environment on the touch input surfaces of a computer keyboard and terminal, particularly in a medical facility setting.

Figure 1:
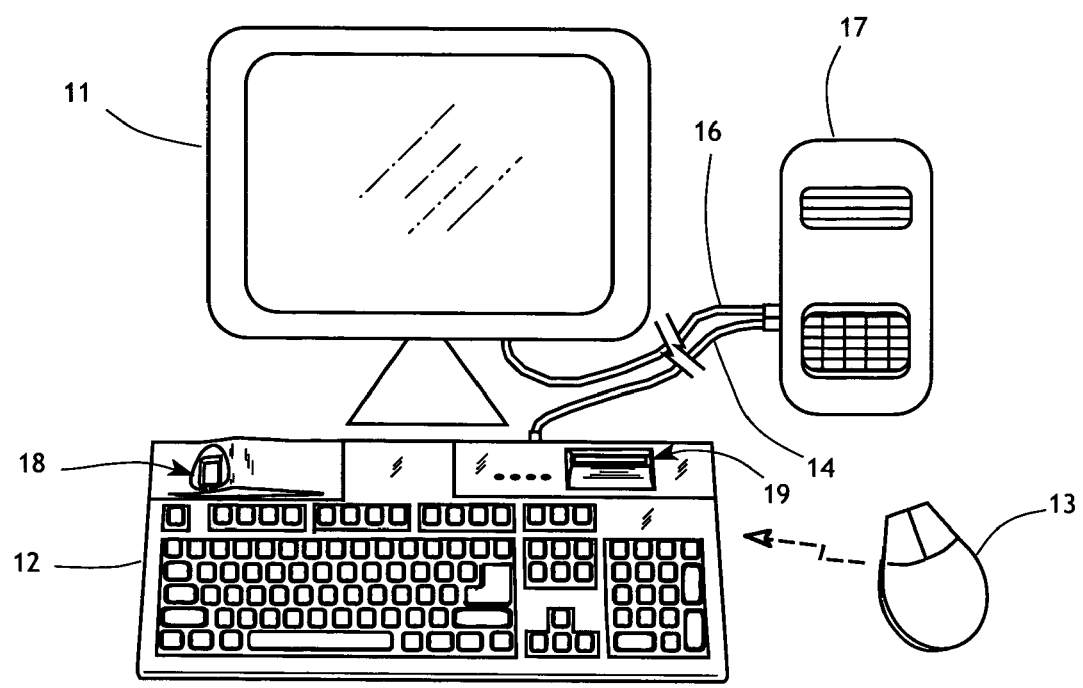
FIG. 1 is a functional diagram depicting a typical prior art computer terminal, including keyboard and other input devices and monitor.

With regard to FIG. 1, a typical computer terminal used in a medical setting such as a hospital, clinic or doctor's office may include a computer monitor 11 that displays the graphical user interface presented to a user by a central computer system, here represented as computer 17. The terminal typically includes a keyboard 12, generally an alphanumeric layout with 40, 60, or more than 100 keys. It may also be combined with an input device 13 such as the mouse shown, or a trackball or joystick or the like, as is known in the prior art. Generally the components 11, and 12-13 are connected to the computer system 17 through cables 16 and 14, respectively. The cable connection is usually a high speed standard data transmission system, such as USB 2.0, which runs as fast as 480 MB/sec, or USB 3.0, which will run as fast as 4.8 GB/sec. The cables may also provide power for the keyboard 12 and mouse 13, which may have a wired or wireless connection to the keyboard.

It is also typical to provide some form of user ID hardware on the keyboard to limit access to the computer system to those individuals who are authorized by the operators of the medical facility. For example, the illustration of FIG. 1 shows a fingerprint scanner module 18 supported adjacent to the key array of the keyboard 18, and a card reader module 19, which may comprise a smart card reader, magnetic stripe car reader, optical scanner, or the like. Other modules which may be incorporated in the keyboard for security purposes may be selected from a group including retinal scanners, facial feature scanners, handwriting analyzers, and the like which are known in the security industry.

It may be appreciated that the cable connections 14 and 16 are typically made to be difficult or impossible to disconnect and reconnect by an average system user. This practice is set to discourage potential hackers or vandals from tapping directly into the computer system through an existing cable connection. Thus the keyboard 12 and input device 13 (hereinafter, keyboard) are typically considered "hot" or 'live', and any touch on the keys may easily provoke a keystroke signal from the keyboard to the computer system. As noted above, there is the potential danger that, when the live keyboard is undergoing an antiseptic wipedown procedure, accidental or random keystrokes may be sent through the system. If appropriate security measures are in place to prevent unauthorized tampering, the keyboard and its associated terminal may be shut down immediately and remain unusable until the terminal is restarted through authorized security protocols.

Figure 2:
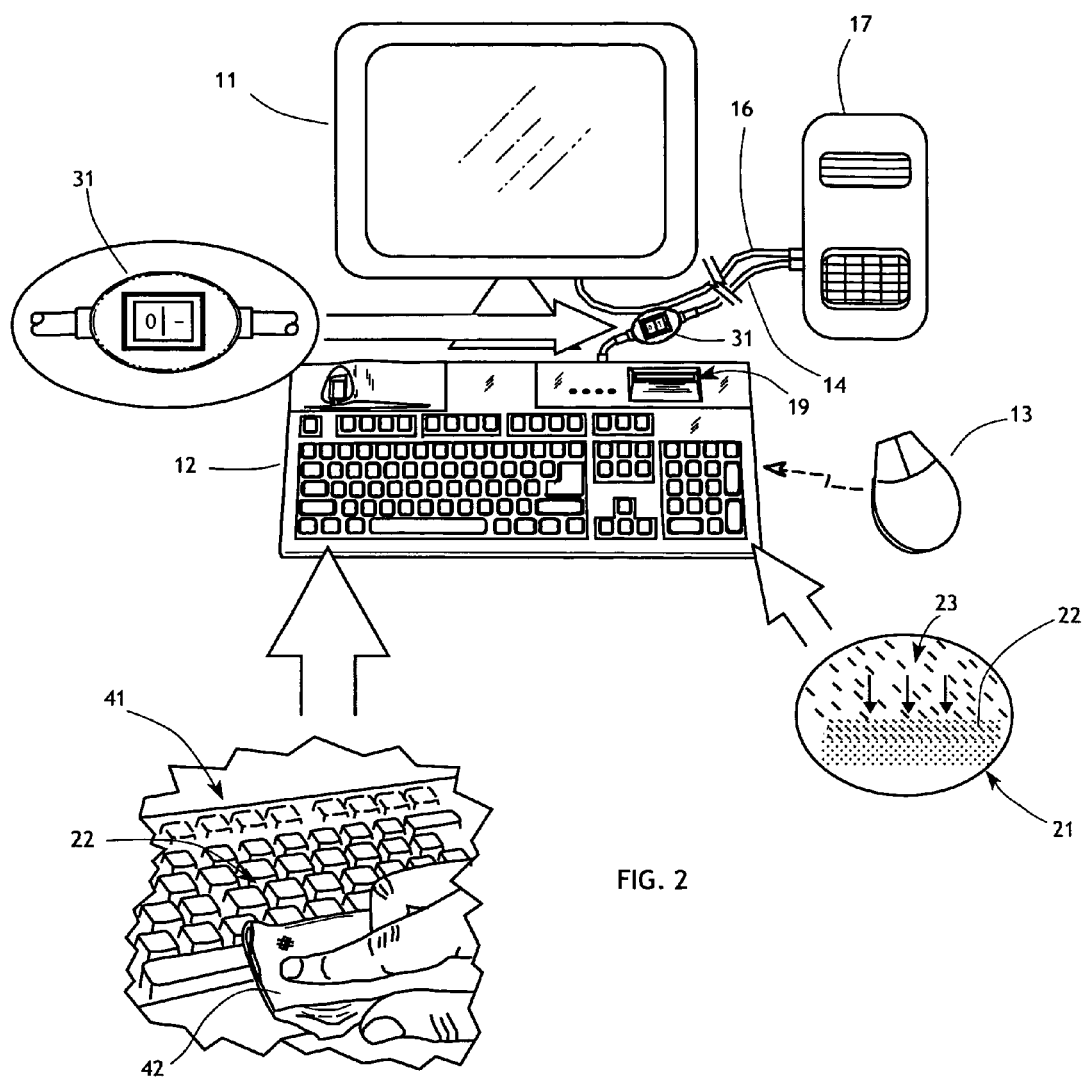
FIG. 2 is a function block diagram depicting the method steps and apparatus that are installed in a typical prior art computer terminal.

With regard to FIG. 2, the invention provides a combination of measures that, taken together, comprise an efficient apparatus and method for managing and assuring the sustained disinfection and cleanliness of the prior art terminal assembly of components shown in FIG. 1. (Note that prior art components that are identical in FIGS. 1 and 2 are labeled with the same reference numerals in both figures.) One measure taken in accordance with the invention is the application of a metal ion treatment 21 to the plastic or polymer substances 22 forming the computer keyboard 12 and other user input devices 13, hereinafter termed the computer keyboard. Generally the metal ions 23, such as Ag, Ti, Zn, or others high on the electromotive series, may be mixed with or impregnated into the material that comprises the keyboard components. One such process involves spraying a solution of silver ions onto the manufactured keyboard components, and thereafter drying them to adhere the ions to the surface of the materials (often polymer plastic or resin). These processes typically adhere the ions or drives the ions sufficiently deep so that subsequent washing or general wear of the keyboard surface cannot remove the surface layer containing the metal ionic treatment. This treatment provides a long-term antimicrobial effect that discourages colony formation and proliferation of bacteria and viruses on the surfaces of the keyboard and input devices. Generally, over the span of a few hours, bacterial contamination on a silver impregnated keyboard will diminish, rather than multiply, since the metal ions are known to inhibit bacterial growth, and diminish the contamination.

Another measure provided by the invention is the installation of a shutoff mechanism such as shutoff switch 31 in the cable 14 that connects the keyboard 12 to the computer 17. The switch 31 may comprise a simple SPST switch that is configured to open the data connections between the keyboard 12 and the host system 17 (although the power conductors of the cable 14 may remain connected if sustained power is required by the keyboard or its ancillary devices, e.g., 13, 18, 19, or the like). When the switch 31 is turned off, any incidental or inadvertent keyboard entries made by a user or maintenance technician will not be transmitted to the host system. When the switch 31 is turned on, the data connections are restored (for example, USB protocols enable such "hot swap" interruptions), and the use of the keyboard may resume. Restart (resumption) after a switch-on transition may require a new security access clearance, using the modules 18 and/or 19 as well as user name and password requirements.

Alternatively, the shutoff mechanism may comprise a key or button on the keyboard 12, an expedient that is known in the prior art. Furthermore, if the keyboard 12 is connected to the computer system 17 via a wireless (RF, IR, etc.) medium, the key or button on the keyboard may be used to cut off and re-establish the wireless connection prior to the wipedown procedure described below.

Another measure taken in accordance with the invention is the periodic and reiterated wipedown 41 of the keyboard 12 and its ancillary devices. Although this procedure is known in the hospital and medical services industries, it has unique advantages in combination with the other steps of the antimicrobial process. The wipedown procedure is typically carried out using a prepackaged, woven or non-woven fabric cloth 42 that is saturated with a hospital-certified antiseptic liquid. (Cloth and liquid may be provided separately.) The entire surface area 22 of the keyboard and its keys, as well as the other devices and surfaces that may be touched by a computer terminal user, is contacted and wiped with the cloth 42 by a medical technician or terminal user. The antiseptic immediately kills virtually all microbial contaminants, rendering the surface sterile at once. It is usually prudent to allow the liquid antiseptic to dry on the surfaces of the keyboard and related surfaces, then the computer terminal is known to be sterile and ready for use once again.

In this anti-microbial system, the person undertaking the wipedown process will first turn off the switch 31 to disconnect the data link through the cable 14. The wipedown is then carried out, the surfaces are allowed to dry, and the switch 31 is turned on to re-instate the keyboard with the host system 17. During the wipedown process, keystroke signals are blocked from being transmitted if any of the keys are inadvertently pressed whilst being cleaned. Thus the installation and use of the switch 31 is a critical feature in enabling easy wipedown procedures without fear of triggering a security alert and shutdown. As noted previously, a security access ID protocol may be implemented upon restart to prevent tampering with the system.

Figure 3:
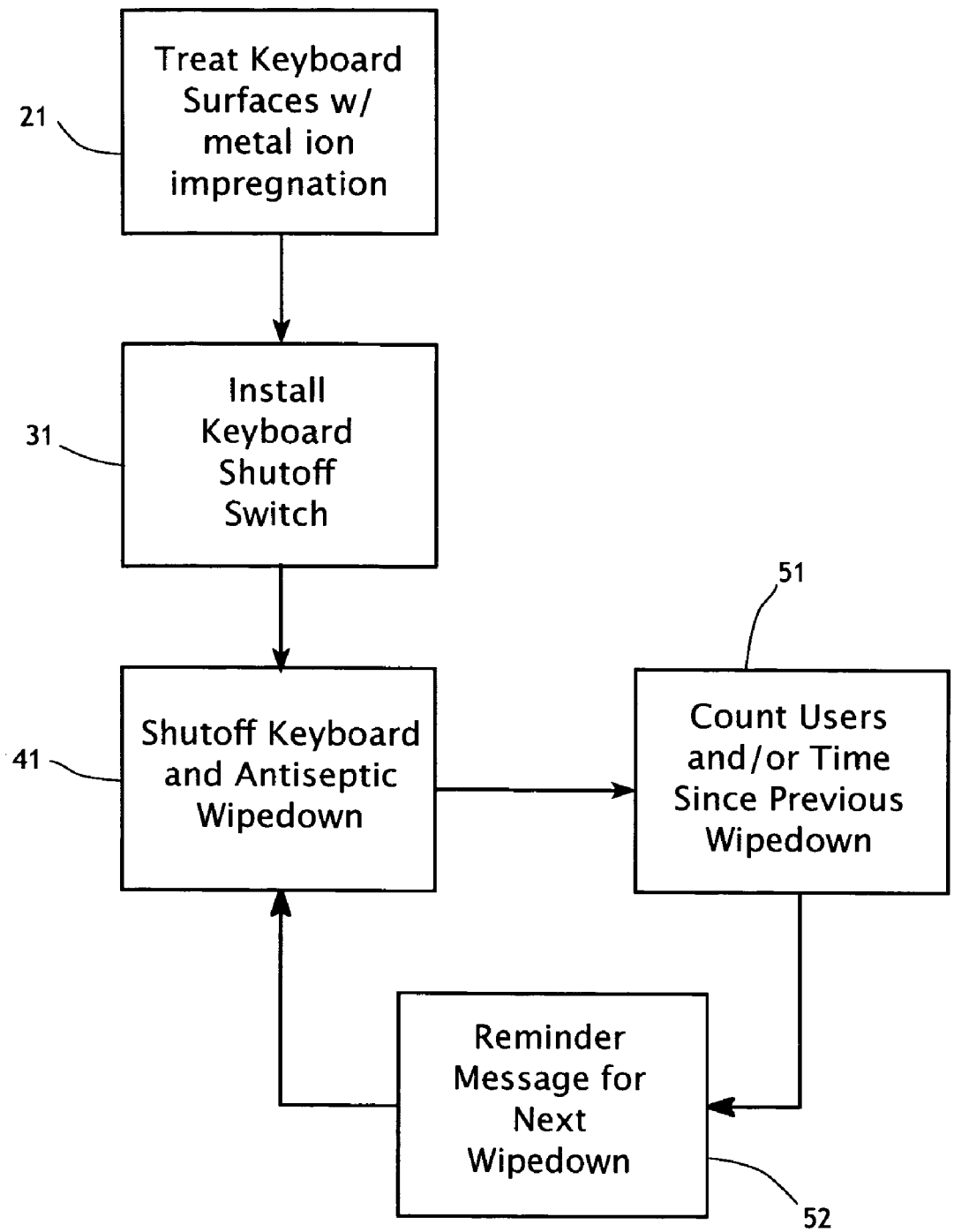
FIG. 3 is a functional block diagram depicting the computer routine that determines the optimum time for calling for another wipedown procedure for the computer keyboard and input devices.

With regard to FIG. 3, the antimicrobial system further includes a method for managing the wipedown procedures in a reiterated manner. Whereas typically terminals are designated for wipedown sterilization on the basis of elapsed time, this approach does not take into consideration actual numbers of users or total time of use, both factors being significant in assessing the potential for surface contamination and the need for immediate sterilization. Based on actual use, there may be a need for less (or more) wipedown procedures.

In the method illustrated in FIG. 3 the steps described previously are carried out, including the metal ion impregnation of the keyboard surfaces, the installation of the shutoff switch 31, and the periodic and repeated wipedown procedures 41 to sterilize the keyboard on an immediate basis. In order to assess the potential bio-contamination of the keyboard surfaces, the computer system 17 to which the computer keyboard 12 is operatively connected may be programmed to estimate the contamination hazard posed by the keyboard 12, based on a counting system. The variable taken as the bio-contamination indicator may be the number of users logged in since the last wipedown procedure, the current site of the keyboard (e.g., hospital ward, laboratory, nurses' station), total time of use, and the dormancy time (elapsed time since previous use). One indicator for identifying the time of a previous wipedown procedure may be the last time that the keyboard switch 31 was shut off. When the computer system's program counts (step 51) a sufficient number of the indicator events or parameters, it then issues a reminder message (step 52) on the display 11 to carry out a wipedown procedure within an allowed time period.

For example, if the computer keyboard 12 has been wiped down and there have been no further users for some time period, the subsequent wipedown procedure 41 may not be warranted or required, and may be postponed. If there number of users logged into the terminal does not reach a threshold level, the next wipedown may be postponed. These parameters may be adjusted for the situation in which the terminal is located or transported, and they enable the computer system to manage the anti-microbial treatments used in the medical facility. As a result, the computer system may optimize the use of wipedown procedures so they are done when necessary, minimizing the maintenance labor and the downtime of the computer terminal. It may also regard the dormancy time and the resulting action of the metal ion treatment to allow the metal ion treatment to function and reduce microbial contamination.

Thus the seemingly disparate elements of the apparatus and method of the invention are tied together by the synergistic manner in which each potentiates the others. The shutoff switch enable easy wipedown sterilization on a short-term basis, and the metal ion impregnation affords long-term antimicrobial action. And the scheduling of the wipedown sterilizations may be managed by the very computer terminal that is being sterilized.

The foregoing description of the preferred embodiments of the invention has been presented for purposes of illustration and description. It is not intended to be exhaustive or to limit the invention to the precise form disclosed, and many modifications and variations are possible in light of the above teaching without deviating from the spirit and the scope of the invention. The embodiment described is selected to best explain the principles of the invention and its practical application to thereby enable others skilled in the art to best utilize the invention in various embodiments and with various modifications as suited to the particular purpose contemplated. It is intended that the scope of the invention be defined by the claims appended hereto.

The invention claimed is:

1. A method for carrying out long-term and short-term disinfection of a computer input keyboard connected via cable or wireless connection to a computer system, including:
    impregnating the computer input keyboard with a metal ion known to have antimicrobial properties, whereby the surfaces of the keyboard actively inhibit microbial growth and persistence;
    installing a shutoff mechanism to interrupt the data link between the computer input keyboard and the computer system;
    carrying out repeated wipedown sterilization procedures on the computer keyboard, each wipedown sterilization procedure being preceded by turning off said shutoff mechanism to prevent keystroke entry during said wipedown sterilization procedure and followed by turning on said shutoff mechanism to restore data communications between the computer input keyboard and the computer system.

2. The method of claim 1, wherein said metal ion is selected from the group consisting of: Ag, Ti, and Zn.

3. The method of claim 1, further including the step of the computer tracking the usage of the computer input keyboard and requesting a wipedown sterilization procedure when a usage threshold is reached.

4. The method of claim 3, wherein said step of tracking the usage of the computer input keyboard includes counting the number of users of the keyboard since the previous wipedown sterilization procedure.

5. The method of claim 3, wherein said step of tracking the usage of the computer input keyboard includes counting the total time of use of the keyboard since the previous wipedown sterilization procedure.

6. The method of claim 3, wherein said step of tracking the usage of the computer input keyboard includes counting the elapsed time since said shutoff mechanism was previous turned off for the previously wipedown sterilization procedure.

7. A method for carrying out long-term and short-term disinfection of a computer input keyboard connected via cable or wireless connection to a computer system, including:
    installing a shutoff mechanism to interrupt the data link between the computer input keyboard and the computer system;
    carrying out repeated wipedown sterilization procedures on the computer keyboard, each wipedown sterilization procedure being preceded by turning off said shutoff mechanism to prevent keystroke entry during said wipedown sterilization procedure and followed by turning on said shutoff mechanism to restore data communications between the computer input keyboard and the computer system.

8. The method of claim 7, further including the initial step of impregnating the computer input keyboard with a metal ion known to have antimicrobial properties, whereby the surfaces of the keyboard actively inhibit microbial growth and persistence.

9. The method of claim 7, further including the step of the computer tracking the usage of the computer input keyboard and requesting a wipedown sterilization procedure when a usage threshold is reached.

\* \* \* \* \*